United States Patent [19]

Hermsdörffer et al.

[11] Patent Number: 5,007,433
[45] Date of Patent: Apr. 16, 1991

[54] STIMULATION DEVICE

[75] Inventors: Joachim Hermsdörffer; Günther Galfe; Stefan Lautenbacher, all of München; Reinhard Korte, Göttingen; Hans-Joachim Krause, Göttingen/Elliehausen; Frans Krüll, Göttingen; Arno May, Göttingen; Dietmar Oberdorfer, Göttingen; Ulrich Plüquett, Göttingen, all of Fed. Rep. of Germany

[73] Assignee: Phywe Systeme GmbH, Gottingen, Fed. Rep. of Germany

[21] Appl. No.: 369,720

[22] Filed: Jun. 22, 1989

[30] Foreign Application Priority Data

Jun. 23, 1988 [DE] Fed. Rep. of Germany ....... 3821219

[51] Int. Cl.$^5$ .............................................. A61B 19/00
[52] U.S. Cl. ................................. 128/742; 128/744; 606/29
[58] Field of Search ................................. 606/27–31; 128/399, 736, 742, 897, 744

[56] References Cited

U.S. PATENT DOCUMENTS

| 1,842,323 | 1/1932 | Gluzek | 128/744 |
| 3,533,397 | 10/1970 | Scher | 128/742 |
| 3,933,148 | 1/1976 | Wyler et al. | 128/744 |
| 3,938,526 | 2/1976 | Anderson et al. | 128/399 |

Primary Examiner—Stephen C. Pellegrino
Assistant Examiner—David Shay
Attorney, Agent, or Firm—Thomas, Kerr & Kayden

[57] ABSTRACT

A stimulation device for the determination of the temperature perception of the skin of a patient by means of a stimulator, which is arranged in a casing and which can be heated up or cooled down by a Peltier element. The stimulator (1) is arranged moveably along an axis (5) in the casing (4) and shows a projection (14) in relation to the casing (4) in the starting position. A first pressure device (6) cooperates with said stimulator (1) in such a way that said stimulator (1) can be shifted along said axis (5) by expenditure of force until said projection (14) is at zero. The force is predefined or adjustable by said first pressure device (6).

10 Claims, 4 Drawing Sheets

STIMULATION DEVICE

FIELD OF THE INVENTION

The invention starts out from a stimulation device for the determination of the temperature perception and pain sensation of a patient through cutaneous contact stimulation by means of a stimulator, which is arranged in a casing and which can be heated up or cooled down by a Peltier element.

BACKGROUND OF THE INVENTION

In numerous diseases, as, for example, in diabetic neuropathy, the examination of temperature perception and pain sensation is used for early diagnosis as well as for controlling the courses of disease and therapy. The warm-cold-perception as well as the faculty of perceiving pain caused by heat are examined, both of which reflect the functional status of the little nerve endings. The stimulator is brought into contact with a suitable part of the patient's body. Starting from a mean temperature the temperatures of the stimulator are raised or lowered. The patient states at what time he notices a change in temperature (warm-cold-perception) or when he first feels pain (pain sensation). In a patient with, for example, diabetic neuropathy the warm-cold-perception as well as the pain sensation is shifted to higher values. The same applies to other diseases with an impairment of the thin nerve endings, so that in these cases a diagnosis and therapy valuation can be performed with the above mentioned method.

A stimulation device of the kind described at the beginning is known from a prospectus of the firm Medelec Ltd., entitled "TTT". The stimulator is arranged in and firmly connected to the casing. The Peltier element is heated up or cooled down in correspondence with the direction of the current supplied to the Peltier element. The stimulator is connected to the Peltier element in such a way that the heat is transmitted to the stimulator correspondingly. The stimulation device is brought into contact with a suitable part of the patient's body, for example, with the hand or with the foot. In the following examinations it turned out to be a disadvantage that the test results depend on the bearing pressure of the stimulator. The bearing pressure cannot be adjusted exactly in the devices known up to now. This increases the measuring error, thus reducing the reliability of measurements. The DE-OS 33 09 093 describes a device for measuring the function of blood circulation of the skin, where a certain part of the skin is heated up and the course of temperature is measured on a spot that was not heated up in the midst of the heated-up area. The device comprises a casing, in which a fluid-operated piston supported by a recuperating spring is arranged movably, which carries a component of the Peltier element, thus making the contact of the Peltier element with the patient's skin possible. The reaction force of the pneumatic pressure acting upon the casing requires that the weight of the casing is great enough for this reaction force to develop and that the casing is not lifted from the patient's skin. This construction further requires that the casing can only be put on the patient's skin from the top pointing vertically downwards. A reverse positioning, or even the positioning on a vertical part of the patient, as, for example, on the cheek or on part of the foot, is not possible. In any case, however, the patient is exposed to the considerable weight of the casing, so that, there is the risk that the area to be examined is excessively compressed by this weight leading to a reduced blood circulation of the resp. area and thus, of course, to a distortion of the measuring result.

The DE-OS 29 12 349 describes a device for the determination of the moisture state of the human skin, in which an electrode holder is mounted to a spring and has a projection in relation to a casing and which can be attached to and pressed against the patient's skin against the resistance of the spring, until the projection has disappeared. Obviously, the pressing against the human skin is carried out manually and is therefore variable and not reproducible with regard to the pressure.

SUMMARY OF THE INVENTION

Therefore, the invention has as its objective to further develop a stimulation device of the kind described at the beginning in such a way that reproducible test results can be obtained as far as possible in all positions of use.

According to the invention this object is acheived with the stimulation device of the kind described at the beginning in which the stimulator is arranged moveably along an axis in the casing and shows a projection in relation to the bearing surface of the casing in the starting position, in which a first pressure device is provided for the stimulator and a second pressure device is provided for the bearing surface of the casing, in which the first pressure device cooperates with the stimulator in such a way that the stimulator can be shifted along the axis by expenditure of force until the projection is at zero, with the force being adjustable by the first pressure device, and in which the second pressure device cooperates with the casing in such a way that the bearing surface of the casing can be locked in the direction of the axis by expenditure of a second adjustable force. In this case, the stimulator is no longer firmly mounted to the casing, but arranged moveably along an axis. In the starting position, that is, as long as the stimulator is not brought into contact with the body of the patient, the stimulator shows a projection in relation to the casing, it consequently protrudes to a certain degree from the casing. The pressure device is connected to the stimulator in such a way that a certain force has to be applied for moving the stimulator in axial direction. The force to be applied can be adjusted by the first pressure device. When using the stimulation device, the casing is brought into contact with the selected part of the patient's skin in the respective position, that is, in horizontal or vertical arrangement or in inclined position, by means of the second pressure device. It is important that the casing of the stimulation device is in slight contact with the skin of the patient, that is, that the casing exerts only a relatively slight pressure on the skin. The stimulator is then pressed against the skin of the patient with the predefined force by the pressure device. Thus, it is assured that during all examinations the stimulator lies on the skin of the patient with the predefined pressure, irrespective of the body part of the patient. This reproducible pressure has turned out to be one important precondition for obtaining reproducible test results. Depending on the pressure, not only the thermosensitive nerve endings but also the mechanosensitive nerve endings are more or less activated by the forces of pressure. This costimulation may influence the temperature perception and pain sensation. It also changes the temperature perception, which is used as a measure for diagnostic purposes, as described above. The heat transmission from the stimulator to the skin also depends on the bearing pressure. In the state-of-the-art stimulation devices the bearing pressure depends on numerous parameters, so that finally the test results vary considerably because of that dependence. As opposed to this, in the present invention the bearing pressure is always maintained at a constant value. Even when selecting different body parts, as for example, in measuring the temperature perception on the hands or feet of one or more patients, with the hands and feet being of different shapes, the constant bearing pressure is always guaranteed.

The first pressure device might comprise a spring, which is supported at the one side by the stimulator and at the other side by a stopper arranged in the casing. The use of the spring, preferably of a pressure spring, has the advantage that the spring can be easily manufactured or purchased at a low price. Furthermore, it reliably fulfills the designed task of exerting a certain force on the stimulator. The spring is supported at the one side by the stimulator and at the other side by a stopper which is arranged in the casing. For adjusting the magnitude of the force acting upon the stimulator, the stopper, which is arranged in the casing, can be adjustable, by preference coaxially to the moving direction of the stimulator. This adjustment might be effected by a simple knurled screw, the head of which is outside the casing. The knurled screw then cooperates with the stopper in such a way that by turning the knurled screw the stopper is shifted coaxially to the moving direction of the stimulator. Thus, the spring tension and finally also the magnitude of the force acting upon the stimulator can be adapted to the prevailing conditions. An indicator might be provided showing the force acting upon the stimulator and the position of the stopper, in order to be able to reproduce the force once adjusted at a later date. The indicator might, for example, comprise a window in the casing, through which the respective marking might be read, which is passed by a pointer that is connected to the stopper.

The second presure device might comprise a holding arm swivelling and adjustable in all directions, with the casing being connected to the second pressure device. One end of the holding arm is mounted to a fixed object, as, for example, to a table leg. On the other end of the holding arm the casing is provided, with the second pressure device being arranged between the holding arm and the casing. With the help of the second pressure device the casing is always in contact with the respective part of the patient's body at a nearly constant pressure. This is important, as it guarantees that the casing is indeed in contact with the skin of the patient and that the skin of the patient is exposed to a permanent pressure of the stimulator. The pressure of the casing on the skin can still influence the test results. The pressure of the casing also contributes to the mechanical costimulation and can cause changes in the temperature perception and pain sensation. Besides, in longer examinations a too high pressure of the casing might impair the blood circulation beneath and beside the stimulator, most of all in patients with circulatory disturbances. Due to changes in the temperature of the cutaneous and subcutaneous tissues this results in variations of the sensation intensity. In this respect, the second pressure device together with the holding arm contribute to the reproducibility of the test results.

The second pressure device might comprise a shaft rigidly mounted to the casing, with the shaft being guided moveably in a tube which can be mounted to the holding arm, and a holding device fixing the shaft preferably in the mean position. The holding device can be constructed and arranged in such a way that the shaft can be shifted from the fixed position by expenditure of force. The holding device preferably comprises two pressure springs, with each pressure spring having a bearing on the tube and a second bearing on the shaft, and one pressure spring being relieved as soon as the other is loaded, and vice versa. The holding device may comprise an indicator showing the magnitude and direction of the load acting upon the pressure springs. The arrangement of two pressure springs guarantees that in any case one of the two pressure springs is effective depending on whether the stimulator is in an upside-down or upright position. Prior to bringing the casing into contact with the patient's skin, the indicator can indicate the force caused by the weight in the actual position, that is, upside down or upright, inclined or flat. Subsequently, the casing together with the stimulator are brought into contact with the patient's skin by adjusting the holding arm correspondingly and one pressure spring, for example, is loaded in such a way by shifting the tube in the direction of the casing that the casing lies on the skin of the patient with a certain bearing pressure. The bearing pressure results from the values indicated prior to and after bringing the casing into contact with the skin. Furthermore, this arrangement has the advantage that the patient is not firmly attached to the stimulator or casing and in case of an overheating of the stimulator caused, for example, by damage, the patient can free himself by the right movement.

The dependence of the temperature perception on the cooling rates necessary for the heating up or cooling down procedures turned out to be a further though not that important factor influencing the test results. Most of all the cooling procedure is technically more difficult to execute. The Peltier element can be combined with a liquid-cooled heat exchanger and a second Peltier element for cooling the liquid of the heat exchanger, in order to obtain a cooling rate as stable as possible even in the lower temperature range during the stimulating phase, as well as to make a reset to the baseline possible for re-establishing the conditions prior to stimulation. The cooling capacity is already increased considerably by the arrangement of a liquid-cooled heat exchanger. The second Peltier element is arranged or driven in such a way that the cold side of the Peltier element is in contact with the warm side of the heat exchanger, thus cooling the cooling liquid. Thus, the cooling time can be reduced by half, or the cooling capacity in degrees/sec. can be approx. doubled.

BRIEF DESCRIPTION OF THE DRAWINGS

The invention is further described by examples of preferred embodiments. The drawings illustrate.

DETAILED DESCRIPTION

Figure 1:
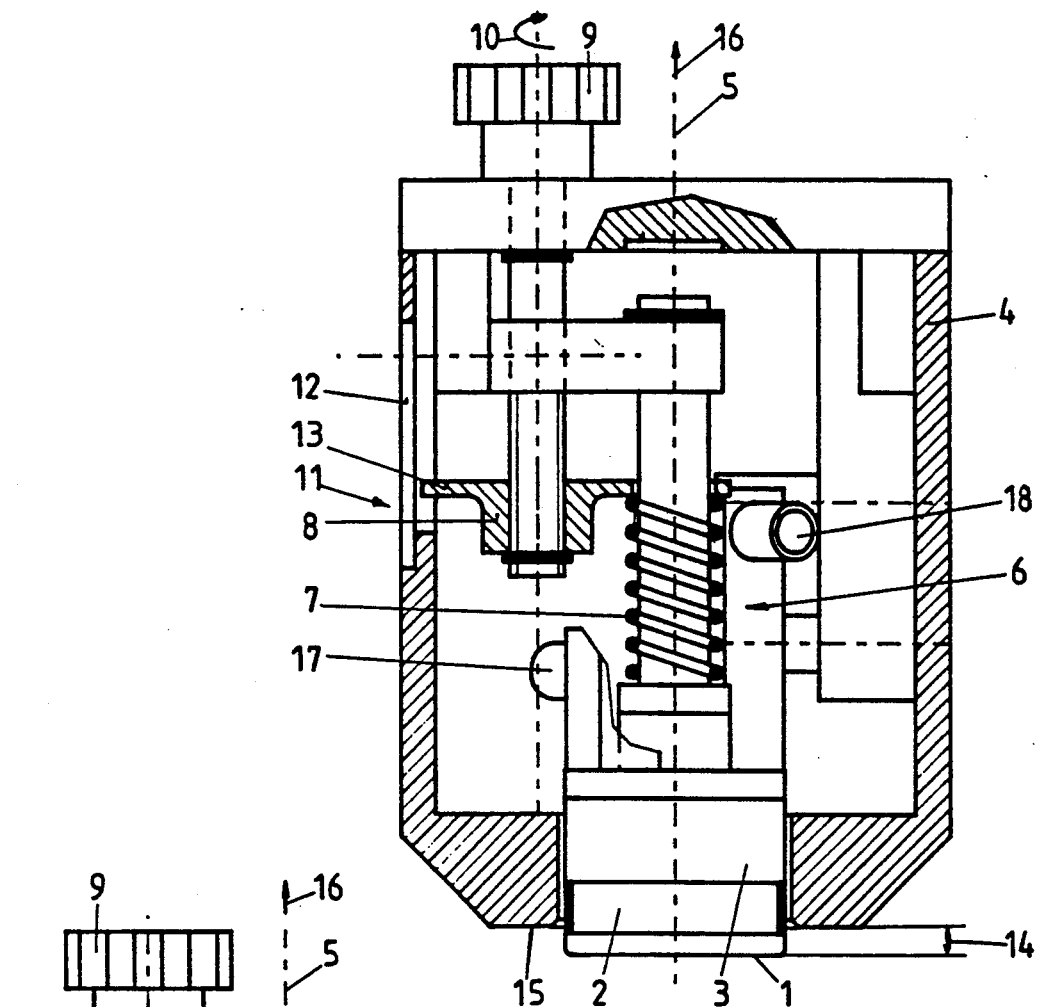
FIG. 1 an embodiment of a stimulation device.

FIG. 1 illustrates the first embodiment of the stimulation device according to the invention. A stimulator 1 is electrically connected to a Peltier element 2. The Peltier element 2 is cooled by a heat exchanger 3, which is also connected to the Peltier element. The stimulator 1, the Peltier element 2 and the heat exchanger 3 are arranged in a casing 4 in such a way that the stimulator 1, the Peltier element 2 and the heat exchanger 3 can be shifted along an axis 5. The shifting occurs against the force of a pressure device 6 comprising a spring 7 and a stopper 8. The stopper 8 can be adjusted coaxially to the axis 5 by means of a knurled screw 9, so that the spring 7 can be adjusted. The head of the knurled screw 9 is outside the casing 4, whereas the thread of the knurled screw 9 cooperates with a corresponding thread with the stopper 8. For adjustment of the stopper 8 the knurled screw 9 is turned in the direction of an arrow 10, which makes the stopper 8 relieve the spring 7. By turning the knurled screw 9 in the opposite direction of the arrow 10, the spring 7 is loaded. An indicator 11, basically comprising a window 12 and a pointer 13 as well as a marking (not shown), serves for indicating the respective position of the stopper or the adjusted tension of the spring 7. In an unloaded condition, that is, as long as the stimulation device is not brought into contact with the skin of a patient, the stimulator 1 shows a projection 14 in relation to the casing 4.

In the following the way of functioning of the stimulation device is described. For the examination of the temperature perception the stimulation device is pressed against the skin of the patient (not shown) in such a way that a basically flat contact area 15 of the casing 4 lies on the skin of the patient. The stimulator 1 is shifted in the direction of an arrow 16 along the axis 5 against the force of the spring 7. The spring 7 is supported at the one side by the stopper 8 and at the other side by the stimulator 1 or the heat exchanger 3. The tension of the spring 7 is adjusted by turning the knurled screw 9 and the position or tension of the spring 7 can be read on the indicator 11. Thus, it is assured that the stimulator 1 is always in contact with the skin of the patient at the same reproducible pressure. The following heating up or cooling down of the stimulator 1 is performed by adequate current supplies (not shown) of the Peltier element 2. The heat exchanger 3 is in conducting connection with the warm side of the Peltier element 2, in order to obtain the shortest possible cooling time or the greatest possible rate of cooling. In its inner part the heat exchanger 3 has a number of ribs to obtain an optimum heat transfer. The cooling liquid is supplied to the heat exchanger 3 via a feeding 17 and let off via an outlet 18.

Figure 2:
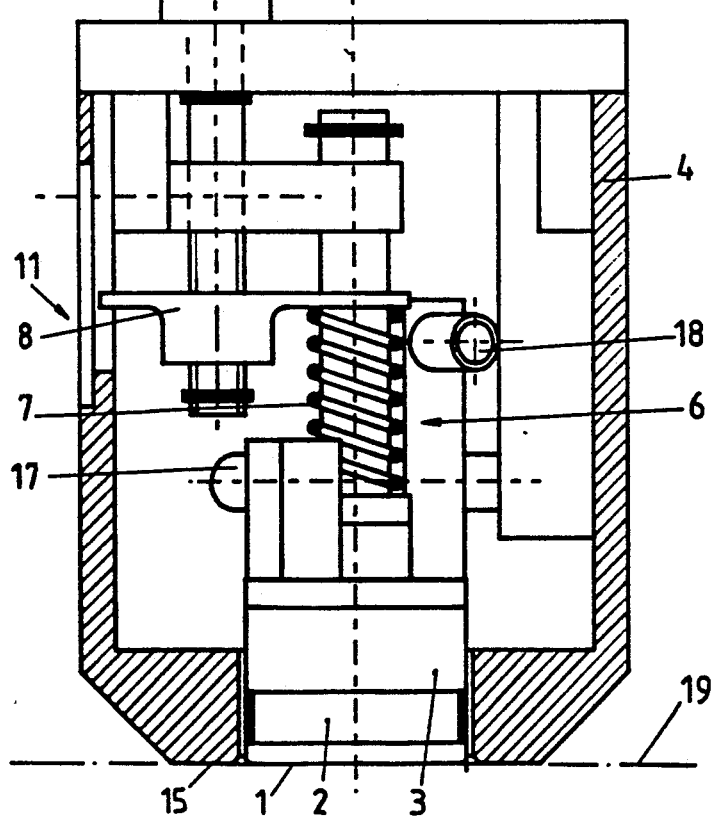
FIG. 2 the stimulation device according to FIG. 1 after being brought into contact with the skin of a patient, FIG. 3 a holding arm with a second pressure device for the stimulation device, FIG. 4 a diagrammatic view of a cooling cycle, and FIG. 5 an arrangement of the pipes of the cooling cycle.

The stimulation device according to FIG. 2 basically differs from the one of FIG. 1 in that the stopper 8 is adjusted to a different position by means of the knurled screw 9, that is, the tension of the spring 7 has been changed. The spring 7 is shown in a compressed state, that is, in the state in which the contact area 15 is in contact with the skin of the patient and thus, the stimulator 1 or rather its outer surface is on the same level 19 with the contact area 15. In this illustration the stimulator 1 is exposed to a force exerted by the spring 7 and adjusted by the pressure device 6 against the direction of the arrow 16. The magnitude of the force can be changed by adjusting the stopper 8 by means of the knurled screw 9, so that in any position, horizontal or vertical arrangement or inclined position, a compensation of the dead weight of the parts connected with the stimulator 1 occurs and a change in the bearing pressure of the stimulator 1 becomes possible to a certain degree. Thus, it becomes possible to obtain an always reproducible bearing pressure of the stimulator 1 and to adjust the bearing pressure to the prevailing conditions.

Figure 3:
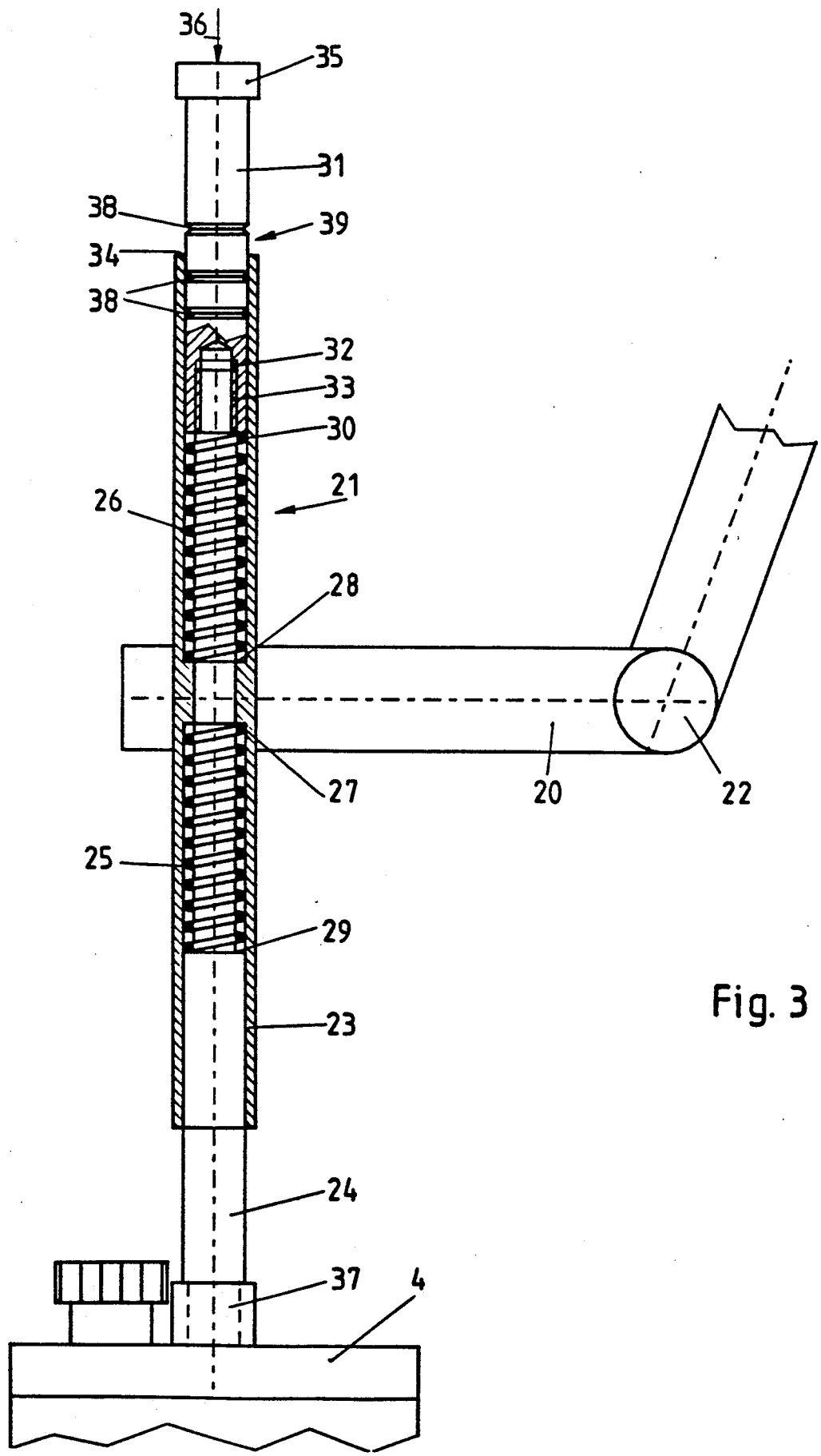

FIG. 3 illustrates the part of a holding arm 20 to which a second pressure device 21 is mounted. The holding arm 20 has a number of joints 22 making it swivelling and adjustable in all directions. The second pressure device 21 is firmly mounted to one end of the holding arm 20. The second pressure device 21 has a tube 23 in which a shaft 24 is guided, which is firmly connected to the casing 4. A first pressure spring 25 and a second pressure spring 26 are provided keeping the shaft 24 in a mean position. The pressure springs 25 and 26 are each supported by a bearing 27 and 28, respectively, of the tube 23 and by a bearing 29 and 30, respectively, of the shaft 24. The bearing 29 is formed by reducing the diameter of the shaft 24, the bearing 30 is formed by screwing an extension piece 31 on the shaft 24. The extension piece 31 has a thread 32 which cooperates with the corresponding counterthread 33 of the shaft 24. The axial extension of the extension piece 31 is selected in such a way that the extension piece 31 projects from one end section 34 of the tube 23. At the end of the extension piece 31 opposite to the thread 32 a stopper 35 is provided, limiting the axial movement of the shaft 24 in the tube 23 in the direction of an arrow 36. In the opposite direction of the arrow 36 a second stopper 37, which is mounted to the casing 4, serves as limitation. The extension piece 31 has notches 38 in the region of the end section 34 of the tube 23, which together with the end section 34 serve as indicator 39 for the actual position of the shaft 24. The shaft is firmly connected to the casing 4 by the stopper 37.

For the performance of the examinations the holding arm 20 is swivelled and adjusted in its joints 22 in such a way that the casing 4 or rather the stimulator 1 is directed towards the part of the patient's body on which the stimulator 1 is to be laid. At this moment, that is, when the casing 4 or rather the stimulator 1 is not in contact with the skin of the patient, the position of the shaft 24 or of the extension piece 31 in relation to the tube 23 is read from the indicator 39. This depends on the position of the casing 4, that is, whether the casing 4 is orientated in the direction of the arrow 36 or in opposite direction of the arrow 36, in a vertical or inclined position to the arrow 36. This is because of the weight acting in the direction of the arrow 36. Correspondingly, one of the pressure springs 25 or 26 is loaded and the respective other pressure spring 25 or 26 is relieved. The casing 4 and thus the stimulator 1 is now adjusted by the holding arm 20 in such a way that the casing 4 or rather the bearing area 15 of the casing 4 comes into contact with the patient's skin at the predefined bearing pressure. The prevailing bearing pressure is indicated by the indicator 39 in connection with the value read at the beginning. Thus, it is guaranteed that the casing 4 is always in contact with the respective part of the patient's body at the same predefinable bearing pressure. Furthermore, it is an advantage that in emergency cases, for example, if the stimulator 1 reaches a high temperature, the patient can free himself from the stimulator 1 by pushing the stimulator 1 and the casing 4 against the direction indicated by arrow 36. The sophisticated arrangement of the doubly acting spring system, that is, the arrangement of the pressure springs 25 and 26, each acting in one direction, holds the shaft 24 in mean position thus ascertaining a freedom of movement in both directions and furthermore, there is the advantage that the casing 4 and the stimulator 1 can be used in any position. One and the same bearing pressure is obtained on the hand of a patient, that is, with the casing in an upside-down position, as well as on the foot of a patient. Of course, this applies also to any other intermediate position.

Figure 4:
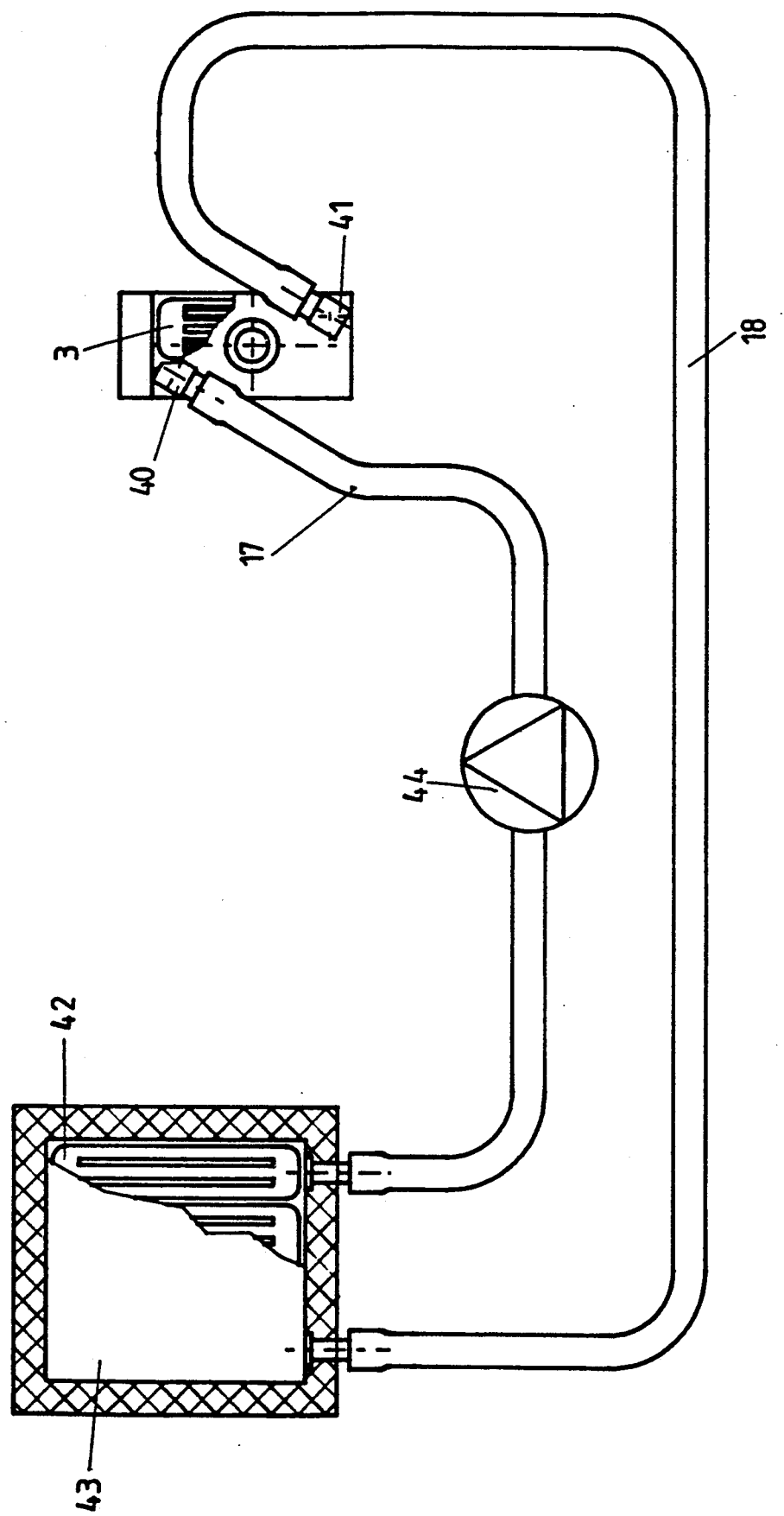

FIG. 4 is a diagrammatic view of the cooling cycle of the stimulation device. The outlet 18 and the feeding 17, which are made of flexible material, are connected to the heat exchanger 3 by a connecting sleeve 40 and 41, respectively. At the other end of the feeding 17 or outlet 18 a second heat exchanger 42 is provided, which is in conducting connection with the second Peltier element 43. The second Peltier element 43 is arranged and fed in such a way that its cold side is adjacent to the heat exchanger 42 thus effecting an additional cooling. For the transport of the cooling liquid a pump 44 is provided in at least one of the feeding 17 or the outlet 18. The arrangement of the second Peltier element 43 next to the second heat exchanger 42 has the advantage that a great quantity of heat can be carried away within short time thus increasing considerably the cooling capacity of the stimulation device. This is important, as is has been shown that the cooling time has an influence on the test results.

Figure 5:
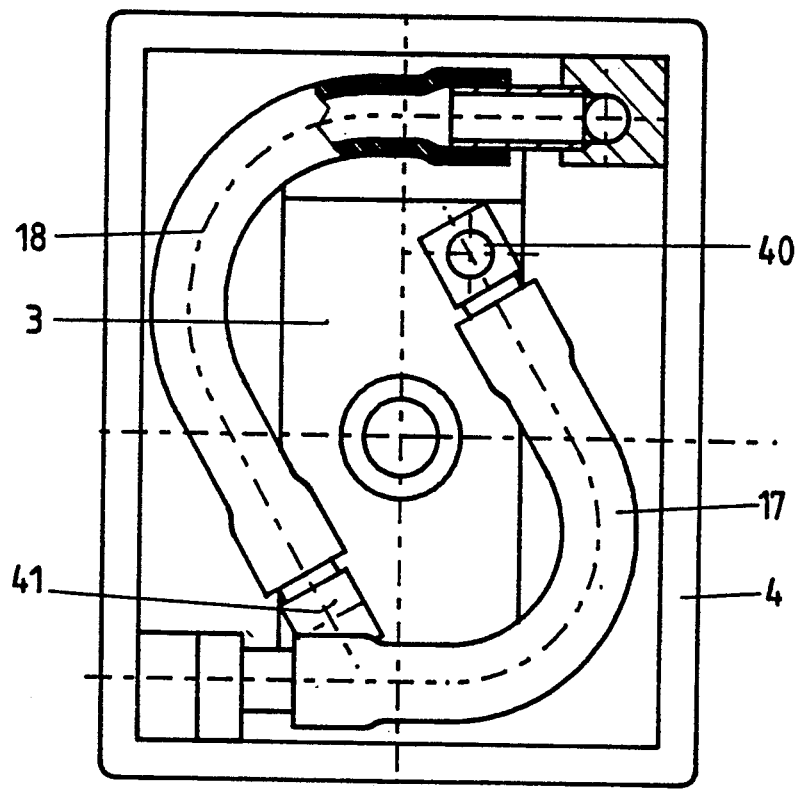

FIG. 5 illustrates again the connecting sleeves 40 and 41 of the heat exchanger 3. The connecting sleeves 40 and 41 are constructed in such a way that the forces caused by the dynamic pressure of the liquid act on one level vertically to the arrow 16, see FIG. 2, that is on the plane of projection in correspondence with FIG. 5. This is because the connecting sleeves 40 and 41 have an L-shape, with one leg of the connecting sleeves 40 and 41 lying in the plane of projection of FIG. 5 and being used as feeding, whereas the other leg is arranged vertically to the plane of projection and is connected to the heat exchanger 3. This has the advantage that, for example, variations in the speed of the cooling agent, which might be caused by different positioning of the stimulation device, have hardly any effect in the direction of the axis 5, that is, do not influence the pressure of the stimulator 1. This measure also serves for keeping the pressure of the stimulator 1 at a constant value and for making it reproducible and therefore it also helps to guatantee the repoducibility of the test results.

Although the invention has been disclosed herein by referring to preferred embodiments thereof, it will be understood by those skilled in the art that variations and modifications of the disclosed embodiments can be made without departing from the spirit and scope of the invention as set forth in the following claims.

LISTING OF REFERENCE NUMBERS

1 = stimulator
2 = Peltier element
3 = heat exchanger
4 = casing
5 = axis
6 = pressure device
7 = spring
8 = stopper
9 = knurled screw
10 = arrow
11 = indicator
12 = window
13 = pointer
14 = projection
15 = bearing area
16 = arrow
17 = feeding
18 = outlet
19 = level
20 = holding arm
21 = second pressure device
22 = joint
23 = tube
24 = shaft
25 = pressure spring
26 = pressure spring
27 = bearing
28 = bearing
29 = bearing
30 = bearing
31 = extension piece
32 = thread
33 = counterthread
34 = end section
35 = stopper
36 = arrow
37 = stopper
38 = notch
39 = indicator
40 = connecting sleeve
41 = connecting sleeve
42 = heat exchanger
43 = second Peltier element
44 = pump.

We claim;

1. A stimulation device for the determination of the temperature perception and pain sensation of a patient by cutaneous contact stimulation comprising a casing including a bearing surface for engaging the skin of the patient, a stimulator received in said casing adjacent the bearing surface of said casing and a Peltier element for changing the temperature of said stimulator, characterized in that the stimulator (1) is arranged moveably along an axis (5) in the casing (4), a first pressure means (6) for biasing with a force of a predetermined magnitude said stimulator toward a starting position in which the stimulator protudes a predetermined distance (14) from said casing beyond said bearing surface (15), and a second pressure means (21) for supporting said casing and biasing the bearing surface of said casing toward the skin of the patient with force sufficient to retract said stimulator by moving said stimulator in a direction toward into said casing to a position in which the protruding portion of said stimulator becomes substantially coextensive with said bearing surface.

2. A stimulation device according to claim 1, characterized in that said Peltier element (2) is combined with a liquid-cooled heat exchanger (3), and in that a second Peltier element (43) is provided for cooling the liquid of said heat exchanger (3, 42).

3. A stimulation device according to claim 1, characterized in that said first pressure means (6) comprises a spring (7), which is supported on one end portion thereof by said stimulator (1), and a stopper (8) mounted in said casing (4) in a position on the other side of said spring and supporting the other end portion of said spring.

4. A stimulation device according to claim 3, and further including means (9) for adjusting the position of said stopper (8) in said casing (4) with respect to the moving direction of said stimulator (1), in order to change the magnitude of the force acting upon said stimulator (1).

5. A stimulation device according to claim 4 characterized in that said casing includes an indicator (11) showing the bias force acting upon said stimulator (1) and the position of said stopper (8).

6. A stimulation device according to claim 1, characterized in that said second pressure means (21) comprises a holding arm (20), and means for adjusting and swivelling said holding arm in several attitudes so as to enable application of the bearing surface (15) of the casing (4) at several attitudes against the skin of the patient.

7. A stimulation device according to claim 6, characterized in that said second pressure means (21) comprises a tube (23), a shaft (24) telescopically received in said tube and rigidly mounted to said casing (4), said tube (23) being mounted to said holding arm (20), and spring means for (25 and 26) biasing said shaft (24) toward a predetermined position with respect to said tube (23).

8. A stimulation device according to claim 7, characterized in that said spring means (25, 26) are constructed and arranged in such a way that said shaft (24) can be shifted from the predetermined position by expenditure of force.

9. A stimulation device according to claim 8 characterized in that said spring means (25, 26) comprises two coil compression springs (25, 26), with each spring (25, 26) bearing at one one end thereof (27, 28) on said tube (23) and bearing at another end thereof (29, 30) on said shaft (24), whereby one spring (25, 26) is relieved as soon as the other is loaded, and vice versa.

10. A stimulation device according to claim 9, characterized in that said second pressure means (21) comprises an indicator (39) showing the magnitude and direction of the load acting upon said springs (25, 26).

* * * * *